United States Patent [19]

Widrow

[11] Patent Number: 4,537,200

[45] Date of Patent: Aug. 27, 1985

[54] ECG ENHANCEMENT BY ADAPTIVE CANCELLATION OF ELECTROSURGICAL INTERFERENCE

[75] Inventor: Bernard Widrow, Stanford, Calif.

[73] Assignee: The Board of Trustees of the Leland Stanford Junior University, Stanford, Calif.

[21] Appl. No.: 512,191

[22] Filed: Jul. 7, 1983

[51] Int. Cl.³ .............................................. A61B 5/04
[52] U.S. Cl. .................................................. 128/696
[58] Field of Search ................ 128/695, 696, 419 PG, 128/704; 364/724

[56] References Cited

U.S. PATENT DOCUMENTS

| | | | |
|---|---|---|---|
| 4,038,536 | 7/1977 | Feintuch | 364/724 |
| 4,170,227 | 10/1979 | Feldman et al. | 128/704 |
| 4,243,045 | 1/1981 | Maas | 128/696 |
| 4,245,649 | 1/1981 | Schmidt-Andersen | 128/696 |
| 4,408,615 | 10/1983 | Grossman | 128/696 |

OTHER PUBLICATIONS

Lee et al., "I.E.E.E. Transactions on Acoustics, Speech and Signal Processing", vol. 29, No. 3, Jun. 1981, pp. 627-641.

Primary Examiner—William E. Kamm
Attorney, Agent, or Firm—Flehr, Hohbach, Test, Albritton & Herbert

[57] ABSTRACT

A technique utilizing a combination of adaptive noise cancelling and conventional signal processing is developed to enhance electrocardiographic monitoring in the operating room by reducing the noise interference that is created by an electrosurgical instrument. Significant amounts of interference are eliminated by radio frequency shielding, passive and active lowpass filtering and optical isolation. A digital adaptive canceller using the least-mean-square algorithm is used to reduce the remainder of the interference, yielding an improvement in signal-to-noise ratio of approximately 100 dB.

11 Claims, 4 Drawing Figures

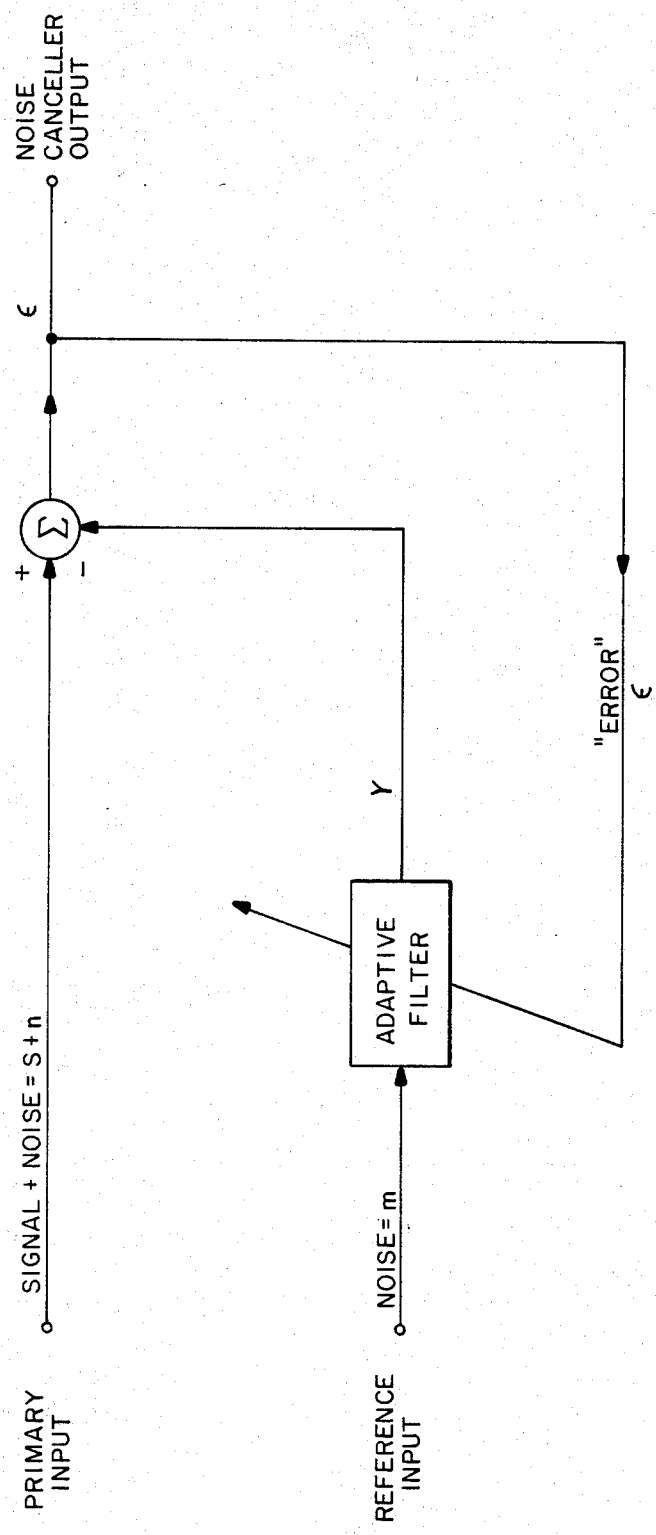
FIG.—1

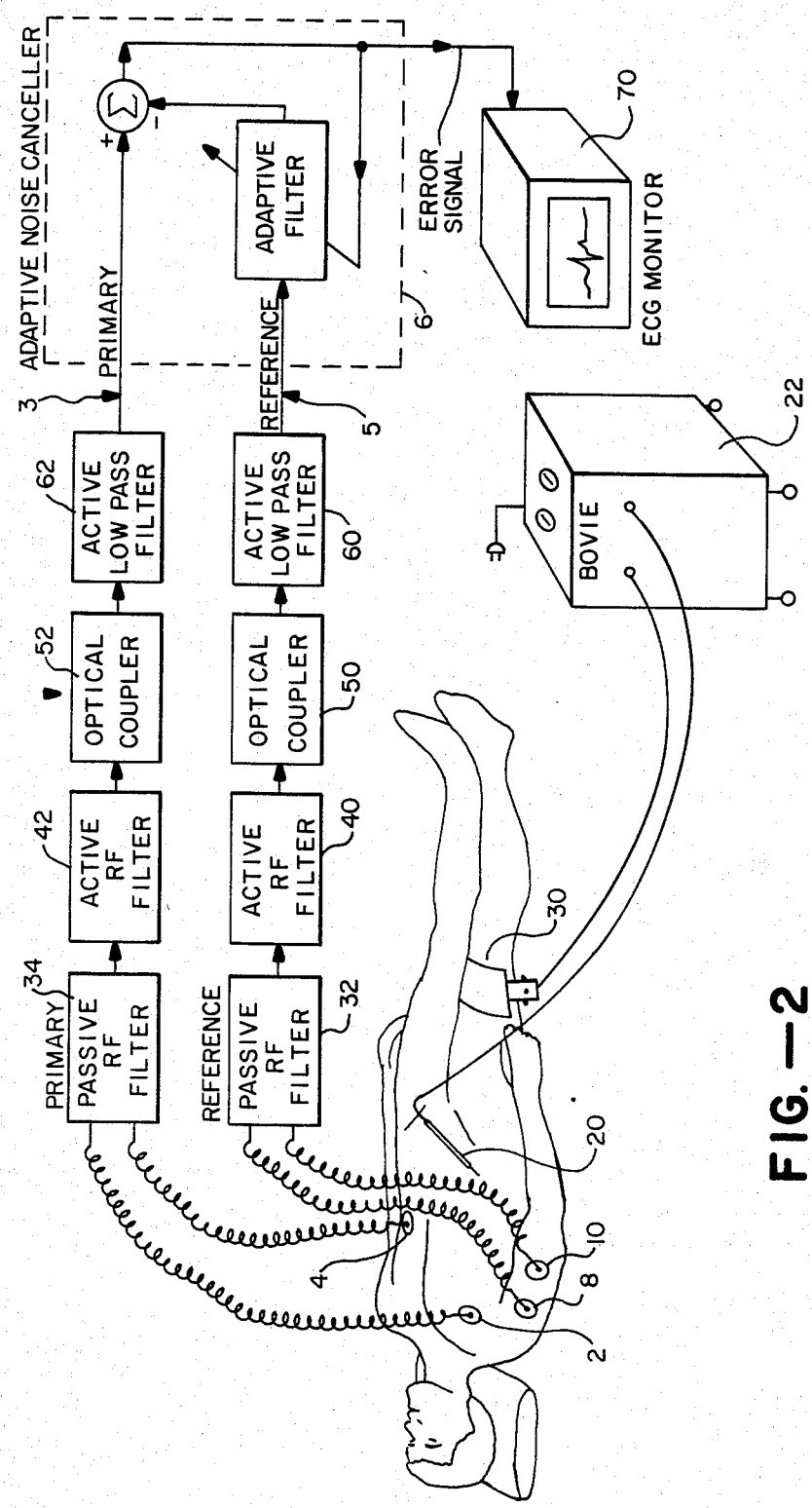
FIG.—2

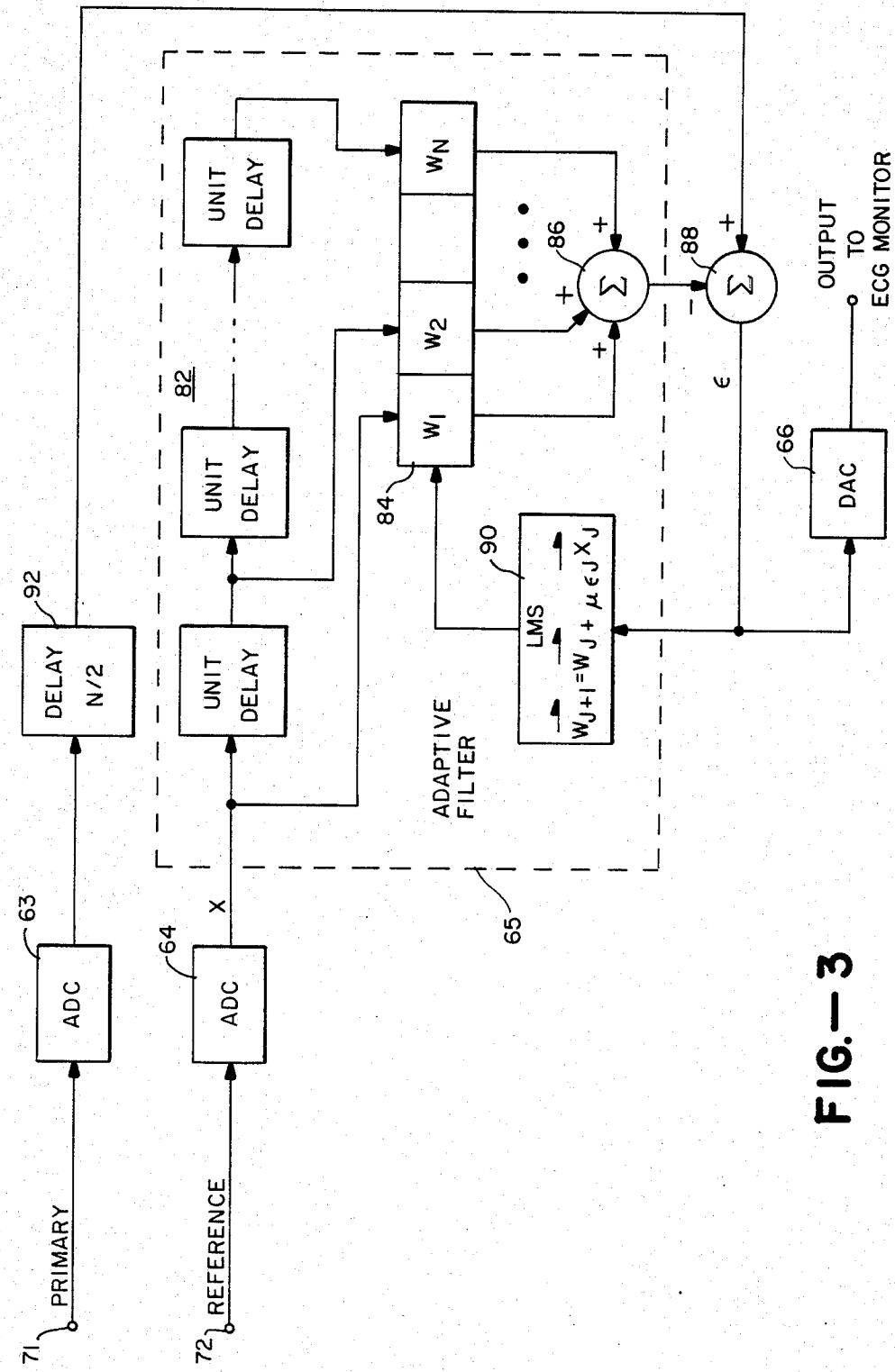
FIG.—3

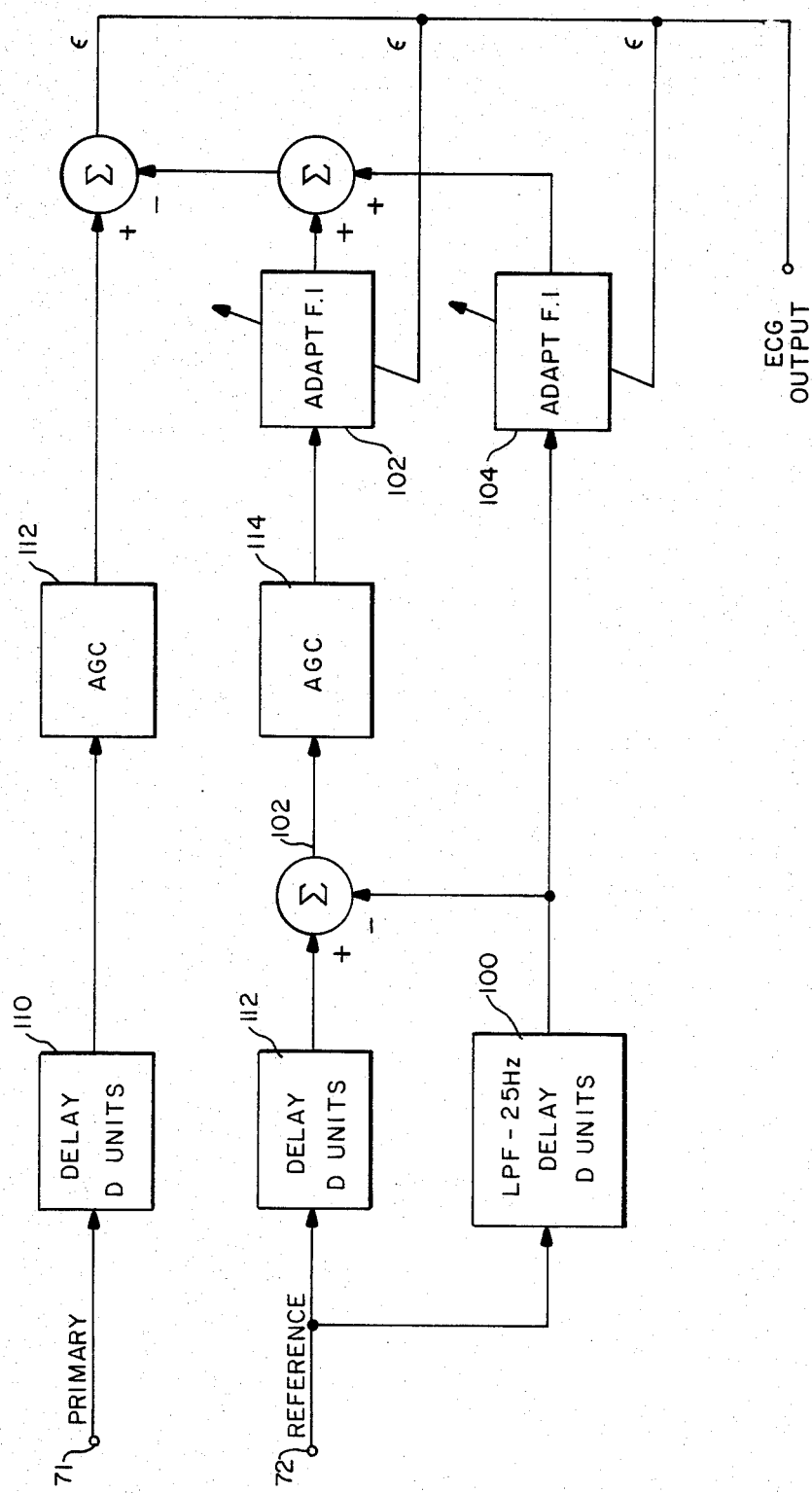
FIG.—4

ECG ENHANCEMENT BY ADAPTIVE CANCELLATION OF ELECTROSURGICAL INTERFERENCE

This invention relates generally to the field of electrical noise suppression and, more specifically, to filtering out and suppressing electrical noise interference in monitors used in the operating room environment.

One of the major sources of operating room interference is the electrosurgical unit ("ESU"). The ESU, often called the "Bovie" after its inventor, is a useful and necessary surgical tool without which many operative procedures would be difficult or impossible to perform. Electrocardiographic ("ECG") monitoring during surgery is also indispensable. However, ECG monitors are impaired by electrical interference generated by the ESU.

The ESU generates a radio frequency ("RF") signal modulated at twice the powerline frequency (120 Hz in the United States). The resultant 100–200 watts of broad-band spectral power is delivered to the point of the surgeon's knife to aid in cutting tissue and coagulating severed blood vessels. The ground return is accomplished by a large area grounding (dispersive) plate that is placed in contact with the patient's back or thigh. During ESU activation, extraordinarily large transient voltages (100–400 volts) are generated ubiquitously over the patient's skin surface. These are caused by the ESU currents passing through tissues of varying shapes, densities and conductivities in reaching the grounding plate. Additional surface voltages are established through parasitic capacitive coupling from the ESU generator to the patient. The magnitude of these voltages is significantly influenced by the power of the ESU output and by the spatial relationship of the ESU and the patient. In addition, in some ESU's, a small but constant low frequency current is passed through the ground plate to assure grounding integrity. Small amounts of patient motion, which change spatial relationships, also induce random low frequency modulation to the entire ECU current.

The ECG electrodes applied to the patient are generally of the silver/silver-chloride type. The ESU noise voltages that appear at the patient's skin surface can cause rectification at these electrodes and can result in demodulation of the burst-type envelope. Thereby, additive nonstationary interference can combine with the ECG waveform in the ECG passband. When the ECG electrodes are placed to obtain the maximum ECG electrical vector, a signal-to-noise ratio of roughly −90 dB exists during periods of ESU activation.

It is a major objective of this invention to enhance the signal-to-noise ratio in this difficult environment so that accurate ECG readings can be obtained.

These and other objectives are achieved by utilizing unique combinations of classical circuit design filtering techniques for the preliminary signal conditioning, and an adaptive filter incorporated in the circuit carrying signals to the ECG to cancel the remaining interference in the passband of the ECG.

The subject of adaptive noise cancelling is introduced and is treated extensively on a theoretical basis in Widrow, et al., "Adaptive Noise Cancelling: Principles and Applications," published in *Proceedings of the IEEE*, Vol. 63, No. 12, December 1975, and incorporated herein by reference. FIG. 1 of this application is a block diagram of an adaptive noise cancelling system. There are two inputs and one output. The "primary" input contains signal plus additive noise. The "reference" input contains noise alone. The primary and reference noises must be uncorrelated with the primary signal, but correlated with each other, if some benefit is to result from use of the noise cancelling. The reference noise is filtered to create a waveform which is a best least-squares estimate of the noise in the primary input utilizing algorithms developed at length in that article. The filtered reference noise is subtracted from the primary input to produce the system output which, in turn, is a best least-squares estimate of the primary signal.

An adaptive filter is needed to perform the function just described, since the relationship of the primary and reference noises is unknown and can be time varying. The adaptive filter produces an output signal that is based on the reference noise input and on a second input, the "error" signal. It automatically adjusts its own internal parameters (which directly control its impulse response) to find the best combination which minimizes the power (mean square) of the error. In the adaptive noise canceller of FIG. 1, the error is obtained from the system output itself. Thus, the entire system adapts in such a way as to minimize its own output power. This causes the output to be a best least-squares estimate of the primary signal.

In the Widrow, et al., article, many applications of adaptive noise cancelling are shown. Biomedical applications that are presented there illustrate how 60 Hz power line interference can be removed from ECG signals, how interference from the maternal heart can be removed from fetal ECG signals, and how electrical signals from a transplanted heart can be separated from the signals generated by the independent beating of the residual atrium of the original heart. However, monitoring of signals with a small signal-to-noise ratio in the operating room presents unusual problems which, to date, were thought to prevent use of this adaptive noise cancelling system in an operating room environment. Further, it has been found that other techniques must be used in combination with the adaptive filter to make it fully effective.

It is a further object of this invention to facilitate the retrieval of ECG from a background of electrical interference; the ECG is the most commonly monitored of the patient's electrical signals.

It is still another object of the invention to provide method and apparatus for screening out interference from an ESU from interfering with the waveforms on an ECG.

To accomplish these objectives, in a preferred embodiment of the invention, filtering, isolation and buffering hardware and techniques are applied to eliminate significant portions of the interfering background noise in the patient monitoring environment. An adaptive filter is used in combination with the above noise reduction techniques to reduce the remaining interfering noise.

FIG. 1 is a block diagram of an adaptive noise canceller, as already described in the prior art.

FIG. 2 is a block diagram of an ECU interference rejection system in accordance with the invention utilizing an adaptive noise canceller.

FIG. 3 is a more detailed diagram of an adaptive noise canceller as designed for use in this invention.

FIG. 4 is a block diagram of an alternative embodiment of an adaptive noise canceller as utilized in this invention.

Referring to FIG. 2, it would seem to follow from the discussion of the use of adaptive noise filters as previously known and understood that primary electrodes 2 and 4 be placed on the patient's body 1 to receive the ECG signal, inevitably corrupted by ESU interference. At the same time, reference electrodes 8 and 10 are placed on the body away from the heart to receive the interference from the ESU while receiving only a minimal amount of ECG signal. It would seem obvious then to connect the primary and reference signals to the adaptive filter as in FIG. 1 and thereby solve the problem. Unfortunately, this solution, as is, will not work.

The primary leads 2 and 4 receive ECG signals in the microvolt range but, as outlined above, they also receive high voltage RF noise (hundreds of volts). Likewise, the reference leads 8, 10 derive high voltage RF noise when the Bovie ESU 20 is energized. It was necessary to first isolate these high voltage RF noises from any and all electronic devices in the system, to make sure that the ECG leads were only connected to high impedance loads, so that essentially no current flowed in them (to prevent nonlinearity or rectification effects at the skin-to-electrode contact points), and to make sure that no new ground paths were possible for the Bovie ESU 20 through the equipment. These requirements posed some difficult electronic problems.

The high power RF current to the ESU 20 comes from an oscillator incorporated in the standard ESU unit 22 whose power supply is not pure dc but, instead, is unfiltered, full wave rectified, power line ac. The result is a suppressed-carrier RF signal, modulated at twice the power line frequency. The ESU circuit itself is simple and well understood. It was developed in its basic form at least fifty years ago; it is explained sufficiently in A. J. McLean, "The Bovie Electrosurgical Current Generator," *Archives of Surgery*, Vol. 18, pp. 1863–73, 1929, incorporated herein by reference. The RF current waveform was designed to be effective for cutting and for cauterization. The power density is greatest between 200 Hz and 50 MHz. However, there is significant power below 200 KHz, and it is this component of the interference that has now been identified as creating the greatest amount of interference.

The basic approach for eliminating the ESU interference is outlined in block-diagram form in FIG. 2. The Bovie power unit 22 is shown connected to the patient's ground plate 30 and to the knife 20 itself. Typical placement of the primary 2,4 and reference 8,10 electrode pairs on the patient's body 1 are also shown. Signals from each of these pairs are first passively filtered at lowpass filters 32,34 to eliminate the gross RF interference. Passive filters in this application were selected to present a high impedance (megohms) loads to the patient electrodes 2,4,8,10. Such filters are, of course, already well known; and their internal circuitry does not comprise an aspect of this invention.

Passive filters 32, 34 were chosen for this "front-end" function since active filters would overload, due to the high RF voltage present on these patient electrodes. After passive filtering, the voltage levels were sufficiently reduced in magnitude and spectral extent that battery-powered active amplification and buffering are then possible, utilizing active lowpass RF filters 40, 42 which are also of standard design.

Optical couplers 50, 52 were used in the next stage to provide isolation, to remove remaining common-mode RF interface, and to prevent new connections from developing between the patient and earth ground. Lowpass active filters 60, 62 followed the optical couplers 50, 52 and were used to eliminate all remaining spectral components above approximately 600 Hz in the primary and reference channels. These filters 60, 62 were powered from the ac line and shared a common ground with the usual ECG monitoring equipment.

At this point, the majority of the ESU noise was removed. However, there still remained strong interference components at 60 Hz, 120 Hz, and 180 Hz, plus other, random, low frequency signals. The effects of higher harmonics were negligible. The magnitudes and phases of the 60 Hz, 120 Hz and 180 Hz interference components varied substantially and rapidly as the surgeon worked with and moved the knife. An adaptive noise canceller 6 was used to remove these remaining nonstationary interference components from the signal.

The adaptive noise canceller 6 delivers performance superior to that of fixed, tuned notch filters. This results from the fact that if the power line frequency changes, the adaptive process sustains notches in the frequency domain exactly where they are needed. In fact, an adaptive system 6 designed for use with a 60 Hz power frequency need not be changed for use with a 50 Hz power supply.

To aid in understanding and application of the invention, details of the system design and the electronic design are presented next. It should be noted that the primary and reference signals are processed substantially identically and in a linear fashion to preserve the linear relationship between their ESU noise components.

The initial filtering of the primary and reference channels 3,5 at the blocks labelled passive RF filter 32, 34 was accomplished using three passive, single-pole, lowpass filters in cascade with 3 dB cutoff-frequencies at 100 kHz, 30 kHz, and 1 kHz, respectively. To prevent high-frequency currents from leaking through these filters, each of the three filter stages was isolated from the other filter stages. The isolation was achieved by placing each stage in a separate copper-clad compartment of a larger copper box. The passive filters were followed by high input impedance, balanced, FET differential amplifiers to ensure a minimum of low frequency current loading at the output of the passive filters which, in turn, ensured only small low frequency currents through the ECG electrode pads attached to the patient. Thus, the linear coupling characteristic of the pads was retained and rectification at the pads was minimized. Additionally, all signals were referenced to a common point (the ECG pad) on the patient's body. This reference point floated with respect to earth ground; thus, it maintained patient isolation. Such isolation eliminated the possibility of accidental skin burns at the ECG electrodes.

The isolated signals were coupled to the remaining earth-ground referenced circuits by using the optical couplers 50, 52. Hewlett-Packard 5082-4354 optical isolators were the specific devices employed. The 5082-4354's, normally nonlinear devices, were used in a circuit configuration that employed optical feedback to achieve one percent (1%) nonlinear distortion. The optical isolator and differential amplifiers were also shielded in separate copper-clad compartments to prevent transfer of RF common-mode leakage currents to the output of the patient isolation stage.

The optical isolators 50, 52 were followed by three-pole, linear-phase (Bessel) lowpass filters 60, 62 with a cutoff frequency of about 600 Hz. The linear-phase characteristic was maintained at low frequencies to preserve the important phase relationships of the ECG. Referring to FIG. 3, the primary and reference lowpass output signals were then fed through analog-to-digital converters 63, 64 ("ADC") into an LSI 11/03 minicomputer 65 where the adaptive filtering was performed in accordance with the algorithms fully described in the incorporated Widrow article. The resulting output was then fed through a digital-to-analog converter ("DAC"), FIG. 3, to a conventional analog ECG monitor 70, shown in FIG. 2.

A block diagram of the adaptive filter is shown in FIG. 3. The reference input was fed into a tapped delay line 82 where successive inputs were individually weighted 84 and summed 86 to form a best least-squares estimate of the ESU noise that remained in the primary. The resultant ECG estimate that was obtained from subtraction 88 of the two signals was used to update 90 the weighting values in the tapped delay line, utilizing the least-mean-squares ("LMS") algorithm:

$$W_{j+1} = W_j + 2\mu\epsilon_j X_j,$$

where
- $W_j$ is a weighting vector;
- $\epsilon_j$ is the error signal;
- $\mu$ is an adaptation constant;
- $X_j$ is an input signal vector; and
- $j$ is the digital time index.

The equation is described in the referenced Widrow article. Other LMS algorithms well known in the literature could also be used to update the weights, in addition to the above method.

The delay 92 in the primary path permits a causal adaptive impulse response to behave very much like a delayed version of a noncausal impulse response in the event that a noncausal impulse response would be advantageous. It should be realized that this specific adaptive filter could be replaced by any filter of variable impulse response with means provided to adjust the impulse response to minimize an average measure of the error such as the mean magnitude, or the mean square, or the mean fourth, etc. Minimum mean-square-error adaptive lattice filters of the type described by Morf and Lee could also be used in this application. The subject is treated extensively in the paper, "Recursive Least Squares Ladder Estimation Algorithms," *IEEE Transactions on Acoustics, Speech and Signal Processing*, Vol. 29, No. 3, pp. 627–641, by D. T. Lee, M. Morf and B. Friedlander, and incorporated herein by reference.

Low frequency (25 Hz) additive distortion was found to be present in the primary and reference inputs 71, 72 and was probably caused by variation in RF current flow as the patient was touched. The low frequency distortion components were particularly troublesome. In some rare instances, these components had rendered overall system performance inadequate. To eliminate these components, a dual reference adaptive noise canceller was developed as shown in FIG. 4. By using a digital lowpass filter 100 with a cutoff frequency of 25 Hz, the reference signal is divided into two components. One component on line 102 consisted of the line frequency distortion at 60 Hz, 120 Hz, 180 Hz, etc., while the other component consisted of only the low frequency distortion below 25 Hz. These two reference signals were then applied to the inputs of two separate but simultaneously working adaptive noise cancellers 103, 104 as shown in FIG. 4. The delay lines 110, 112 of D units in FIG. 4 are used to equalize these lines with the delay introduced by the causal lowpass filter 100. Typically this delay was about 30 sampling intervals. The main reason for using the dual reference signal components was to be able to separately choose the parameters that controlled the rate of convergence. Automatic gain control ("AGC") circuits 112, 114 were used on the primary and high frequency reference signals to normalize input power, to control dynamic range and thereby to effect an additional performance improvement.

The sampling rate chosen for this implementation was about 400 Hz. Sixteen bit, fixed-point arithmetic with twelve bit analog interfaces was found to be adequate to represent all quantities. The adaptation constants were generally chosen to be between 0.02 and 0.2 with reference input powers normalized to unity.

The system described above has been successfully used to monitor the ECG during periods of ESU energization. The initial signal-to-noise ratio ("SNR") was approximately −90 dB at the ECG pads. The dual reference canceller provided the most useful results, although the single reference canceller also produced adequate results during most periods of ESU operation. A substantial reduction in input noise power (approximately 80 dB) was accomplished in the preliminary filtering stages, i.e., at the outputs of active lowpass filters 60, 62 of the system. Final noise reduction was accomplished by the adaptive filter 6, which provided an additional noise reduction of about 30 dB. The resultant SNR of about +20 dB was more than adequate to discern the heart rate, as well as all of the subcomponents of the ECG wave, such as the P and T waves.

The overall improvement in SNR, as compared to using an electrocardiograph without the system of FIG. 2, is approximately 100 dB. This unusually large improvement by a filtering and noise cancelling system is due to the fact identified by the inventors herein that most of the noise can be separated into several large components, each of which can be eliminated at a different stage of the system by utilizing specially selected circuitry. It is recognized that modifications and improvements to the basic concepts set forth herein may occur to those skilled in the art who study this invention disclosure. Therefore, it is intended that the invention not be limited to the exemplary construction shown and described herein but only by the scope of the appended claims.

What is claimed:

1. In a patient monitoring system, means for improving the signal-to-noise ratio, comprising
   (a) means for detecting primary signals from a patient comprising a desired signal and a noise signal,
   (b) means for detecting a reference signal from the patient comprising substantially only said noise,
   (c) means for filtering said patient originated signals; and
   (d) adaptive filter means comprising
   (i) adaptive means responsive to the reference signal for continuously generating a reference noise signal comprising an estimate of the noise in the primary signal received at an input of said adaptive filter; and
   (ii) means for subtracting said reference noise signal from said primary patient originated signal to provide an accurate representation of said desired signal.

2. A system as claimed in claim 1 wherein each of said primary and reference signal detecting means comprise a separate electrode adapted to be attached to spaced portions of the patient's body.

3. A system as claimed in claim 2 wherein said filter means comprise passive filter means for eliminating RF interference from said patient signal.

4. A system as claimed in claim 3, wherein said filter means further comprise active filter means for filtering out high frequency noise from said patient originated signals, and means for coupling the output of said passive filter means to said active filter means, said passive filter means keeping high voltage RF interference away from said active filters.

5. A system as claimed in claim 2, wherein said adaptive filter means comprises
   (a) a tapped delay line;
   (b) means for summing the output of weighting means receiving said reference signal to establish a filtered reference noise signal;
   (c) means for subtracting said filtered reference signal from said primary patient signal;
   (d) means for feeding back an error signal which comprises the difference between the filtered reference signal and the primary patient signal to said weighting means to modify said weighting; and
   (e) means for supplying the error signal to the patient monitor.

6. A system as claimed in claim 5, wherein said feedback means includes means for modifying the weightings according to the algorithm:

$$W_{j+1} = W_j + 2\mu\epsilon_j X_j,$$

where
   $W_j$ is a weighting vector;
   $\epsilon_j$ is the error signal;
   $\mu$ is an adaptation constant;
   $X_j$ is an input signal vector; and
   j is the digital time index.

7. A system as claimed in claim 2 wherein said means for adaptive filtering is an adaptive lattice filter of the minimum-square-error type.

8. A patient monitoring system as claimed in claim 2 wherein said adaptive filter means comprise a variable impulse response including means for adjusting the impulse response to minimize the mean magnitude of the error, or the mean square of the error, or the mean fourth of the error, or a symmetric function of the error in the output of said filter means comprising filtered patient monitoring signals.

9. A method of reducing noise in signals detected on a patient being monitored, comprising
   (a) connecting a first pair of electrodes to the patient to detect a primary patient signal comprising both interference and a desired signal;
   (b) connecting a second pair of electrodes to the patient in a position to detect a reference patient signal comprising approximately only the interference signal;
   (c) filtering said primary and reference patient signals to reduce RF interference;
   (d) filtering the reference signal to obtain a signal representing the remaining interference component of said primary signal;
   (e) subtracting said remaining interference representing signal from said filtered patient signal to remove interference components from said patient signal.

10. A method as claimed in claim 9 wherein the remaining interference representing signal is continuously generated, and the interference representation is continuously concurrently subtracted from the primary patient signal.

11. A method as claimed in claim 10 wherein the interference representation is adaptively modified to represent the noise signal.

* * * * *